United States Patent
Ichihara et al.

(10) Patent No.: US 9,153,931 B2
(45) Date of Patent: Oct. 6, 2015

(54) LASER APPARATUS AND CONTROL METHOD THEREFOR

(71) Applicant: CANON KABUSHIKI KAISHA, Tokyo (JP)

(72) Inventors: Shigeru Ichihara, Tokyo (JP); Shuichi Kobayashi, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/236,103

(22) PCT Filed: Oct. 10, 2012

(86) PCT No.: PCT/JP2012/076745
§ 371 (c)(1),
(2) Date: Jan. 30, 2014

(87) PCT Pub. No.: WO2013/054939
PCT Pub. Date: Apr. 18, 2013

(65) Prior Publication Data
US 2014/0185634 A1  Jul. 3, 2014

(30) Foreign Application Priority Data

Oct. 14, 2011 (JP) .................. 2011-226959

(51) Int. Cl.
*H01S 3/10* (2006.01)
*H01S 3/082* (2006.01)
(Continued)

(52) U.S. Cl.
CPC . *H01S 3/10* (2013.01); *H01S 3/082* (2013.01); *H01S 3/0823* (2013.01); *H01S 3/106* (2013.01);
(Continued)

(58) Field of Classification Search
CPC ....... H01S 3/082; H01S 3/0823; H01S 3/106; H01S 3/107; H01S 3/10; H01S 3/08054; H01S 3/08059; H01S 3/094038; H01S 3/1066; H01S 3/115; H01S 3/1625; H01S 3/1633; H01S 3/1636
USPC .......................................................... 372/97
See application file for complete search history.

(56) References Cited

U.S. PATENT DOCUMENTS 3,500,233 A * 3/1970 Doyle et al. .................. 372/28
3,605,039 A * 9/1971 Harris et al. .................. 372/23
(Continued)

FOREIGN PATENT DOCUMENTS

JP   3567234   6/2004

OTHER PUBLICATIONS

S. Manohar et al., "Region-of-Interest Breast Studies Using the Twente Photoacoustic Mammoscope (PAM)", *Proc. of SPIE*, vol. 6437, 643702-1 (2007).

*Primary Examiner* — Xinning Niu
(74) *Attorney, Agent, or Firm* — Fitzpatrick, Cella, Harper & Scinto

(57) ABSTRACT

The present invention uses a laser apparatus capable of selecting a wavelength of light to be outputted from a plurality of wavelengths, including: a branching unit which is formed of a polarizer and is configured to branch an optical path formed in a resonator including a reflecting unit having a plurality of fixed reflecting planes and an output mirror, into a plurality of optical paths, thereby forming a common optical path having an end defined by the output mirror and a plurality of optical path branches each having an end defined by any one of the reflecting planes; a laser medium disposed in the common optical path; and a selecting unit configured to select, from the plurality of optical path branches, an optical path branch which corresponds to a wavelength of light to be outputted.

22 Claims, 14 Drawing Sheets

(51) Int. Cl.
*H01S 3/106* (2006.01)
*H01S 3/107* (2006.01)
*A61B 5/00* (2006.01)
*H01S 3/08* (2006.01)
*H01S 3/094* (2006.01)
*H01S 3/115* (2006.01)
*H01S 3/16* (2006.01)

(52) U.S. Cl.
CPC ............ *H01S 3/107* (2013.01); *A61B 5/0095* (2013.01); *H01S 3/08054* (2013.01); *H01S 3/08059* (2013.01); *H01S 3/094038* (2013.01); *H01S 3/1066* (2013.01); *H01S 3/115* (2013.01); *H01S 3/1625* (2013.01); *H01S 3/1633* (2013.01); *H01S 3/1636* (2013.01)

(56) References Cited

U.S. PATENT DOCUMENTS

| | | | |
|---|---|---|---|
| 4,063,106 A | 12/1977 | Ashkin et al. | 359/327 |
| 4,099,141 A * | 7/1978 | Leblanc et al. | 372/93 |
| 5,946,090 A | 8/1999 | Tashiro et al. | 356/326 |
| 6,078,606 A | 6/2000 | Naiman et al. | 372/97 |
| 6,580,732 B1 * | 6/2003 | Guch et al. | 372/18 |
| 6,676,402 B1 | 1/2004 | Early et al. | 431/1 |
| 8,405,389 B2 | 3/2013 | Sugioka et al. | 324/244.1 |
| 8,649,015 B2 | 2/2014 | Ichihara et al. | 356/445 |
| 2004/0066828 A1 * | 4/2004 | Tamaki et al. | 372/92 |
| 2014/0092932 A1 | 4/2014 | Ichihara | 372/100 |
| 2014/0109678 A1 | 4/2014 | Ichihara | 73/655 |
| 2014/0123762 A1 | 5/2014 | Furukawa et al. | 73/655 |

* cited by examiner

LASER APPARATUS AND CONTROL METHOD THEREFOR

TECHNICAL FIELD

The present invention relates to a tunable laser apparatus and a control method therefor.

BACKGROUND ART

Development of a medical photoacoustic tomography apparatus (PAT apparatus) using tunable laser is proceeding (NPL 1). Such a PAT apparatus is expected to be capable of determining whether or not a tumor exists by observing blood vessels gathered around the tumor in a living body and analyzing the function of a tissue by making use of a difference in spectrum between oxidized hemoglobin and reduced hemoglobin.

The PAT apparatus is a measuring apparatus configured to acquire an image by irradiating a measurement site by a nanosecond pulse laser, receiving a photoacoustic wave generated therefrom and then analyzing received signals. Because the intensity of laser light applied to a living body attenuates due to diffusion inside the living body, laser light having a high energy output per pulse is needed particularly when a photoacoustic wave has to be obtained from a part located relatively deep inside the living body such as a breast.

A titanium sapphire laser and an alexandrite laser are solid-state lasers each rendered tunable by using a laser medium having a wide gain band. Wavelength selecting systems for allowing a tunable laser to generate laser oscillation of a desired wavelength include one based on an approach such as to provide a prism, a diffraction grating or a birefringent plate in a laser resonator, and one based on an approach such as to utilize an acoustooptic tunable filter (AOTF) (PTL 1).

In cases where the prism is used, a light beam is allowed to resonate in a resonator correspondingly with an angular displacement of optical path which is estimated from the refractive index of the prism. When the prism is used as a reflecting mirror of the resonator, the prism is mechanically rotated in the plane of a substrate forming part of the resonator. When a reflecting mirror is used separately from the prism, wavelength selection is also possible by fixing the prism and mechanically rotating the reflecting mirror located correspondingly with an angular displacement of optical path on a wavelength-by-wavelength basis. In cases where the diffraction grating is used as in the case of the prism, wavelength selection is made by mechanically rotating a reflecting mirror in accordance with an oscillation wavelength.

In cases where the birefringent plate is used, wavelength selection is made by mechanically rotating the birefringent plate in such a manner as to maintain the optical axis of a resonating light beam at the angles of its incidence on and outgoing from the birefringent plate.

In cases where the AOTF is used, wavelength selection is made by means of RF signals applied to the AOTF device without using any mechanically rotating system.

CITATION LIST

Patent Literature

PTL 1: Japanese Patent Publication No. 3567234

Non Patent Literature

NPL 1: S. Manohar et al., Proc. of SPIE vol. 6437 643702-1

SUMMARY OF INVENTION

Technical Problem

The PAT apparatus needs to perform laser irradiation with two or more wavelengths in order to detect the difference in spectrum between oxidized hemoglobin and reduced hemoglobin. Because a signal strength to be measured is influenced by measurement conditions including the condition of a living body and the location of measurement, it is preferable to keep constant the measurement conditions other than the wavelengths when signals acquired from the respective wavelengths are compared to each other. When measurement is carried out with a change in wavelength on an oscillation pulse-by-oscillation pulse basis, the influence by movement of the living body is considered to be sufficiently reduced and, hence, measurement is easy with the condition of the living body and the location of measurement being kept constant. Therefore, irrespective of a wavelength tunable system to be used, an angular displacement of optical path and a shift in oscillation wavelength have to be limited even when a change is made in wavelength on an oscillation pulse-by-oscillation pulse basis. It is also necessary for the oscillation output and each of plural selected wavelengths to be kept constant. It is further necessary to ensure long-term stability of members to repeatedly moving when the wavelength tunable system used has a movable structure.

According to study made on the use of a conventional tunable laser apparatus as a laser light source for the medical PAT apparatus with the above-described requirements in view, the following problems arise.

In cases where the conventionally used prism or diffraction grating is used in a wavelength tunable system, the position of a reflecting mirror is controlled by rotation with use of a stage or the like. If a displacement of the rotational position of the reflecting mirror occurs, the oscillation wavelength fluctuates. If a displacement of tilting angle occurs, a resulting misalignment causes the oscillation output to lower. Therefore, it is necessary to move the stage position on an oscillation pulse-by-oscillation pulse basis as well as to maintain the positional precision stably. During laser oscillation, the driving stage has to be held stationary. Therefore, rotation and standstill of the stage are repeated on an oscillation pulse-by-oscillation pulse basis.

In order to endure such repeated driving, a member having high reliability against repeated driving which is estimated in view of friction and wear of the member and the like has to be used in a driving portion of the stage or that of an optical element housing. Even such a highly reliable driving stage, however, is limited in the durability of the member against repeated driving. In order to ensure the output stability of the laser, on the other hand, it is absolutely essential to maintain the thermal stability of the resonator in a usage environment of the laser. An aluminum substrate is typically used as a laser substrate. When a highly durable material other than aluminum is used as the member, it is possible that a difference in thermal expansion coefficient between the materials causes a hindrance to arise in maintaining the thermal stability of the whole resonator.

A wavelength tunable system using the birefringent plate is formed by combining a plurality of birefringent plates and hence is an optical component having large-sized constitutional elements. In changing the wavelength on a pulse-by-pulse basis, repeated rotation and standstill of the birefringent plate raises a difficulty that such a large birefringent plate has to be controlled by rotation at increasing velocity with increasing frequency of the pulse laser. When a deterioration occurs in rotational precision, a problem of a shift in selected wavelength arises. Further, the wavelength tunable system using the birefringent plate is highly costly, which is problematic also.

With the foregoing problems in view, the wavelength tunable system is preferably a system having no mechanically movable structure that brings about a shift in wavelength and an angular displacement of optical path.

Use of the acoustooptic filter (AOTF) as a wavelength tunable system makes it possible to preclude such a mechanically movable structure. The AOTF comprises an acoustooptic crystal and an ultrasound transducer. When an ultrasound wave is excited in an acoustooptic crystal exhibiting birefringence, diffracted light having a specific wavelength corresponding to the frequency of the ultrasound wave is strongly diffracted in such a direction as to satisfy conditions for phase matching between the ultrasound wave, incident light and diffracted light. By varying the frequency (wave number) of the ultrasound wave to be excited, the wavelength of light varies which allows the phase matching conditions to hold. The AOTF is placed inside the resonator, while a reflecting mirror forming part of the resonator is placed at a desired diffracted position. Further, by placing a chromatic dispersion compensation device, such as a prism, between the AOTF and the reflecting mirror, compensation can be made for the wavelength dependence of a diffraction angle. That is, a desired wavelength can be selected by using an RF signal from an RF power source of the ultrasound wave to be applied to the AOTF without the need to rotate the reflecting mirror.

The diffraction efficiency of the acoustooptic device, however, is usually 70% to 80% and may reach 90% at the highest even when primarily diffracted light is used and, hence, the acoustooptic device has a drawback such that a large loss is incurred in the resonator. In order to obtain laser light of a high output intensity by wavelength selection by the AOTF, primarily diffracted light needs to have an enhanced diffraction intensity. With the AOTF, the intensity of primarily diffracted light depends on the RF signal strength which is the intensity of a propagating ultrasound wave. Because an RF signal having a strength of a predetermined value or higher which exceeds the withstand capability of the device cannot be applied to the AOTF, the AOTF is not suitable for an application which requires a high output power. A product having a laser power of 10,000 W/cm$^2$ has been realized by a Q-switch using the acoustooptic device. The PAT apparatus, however, sometimes requires laser light of high pulse energy. The medical PAT apparatus, in particular, often uses a laser apparatus having a pulse width of about 10 nanoseconds. Such a laser apparatus which calls for a high output energy needs to produce an output power equivalent to a laser power of 100 MW/cm$^2$. This means that it is difficult to realize a tunable laser apparatus capable of generating high energy pulse oscillation by using the AOTF.

The present invention has been made with the foregoing problems in view. An object of the present invention is to provide a laser apparatus having a wavelength selecting system with no mechanically movable structure that brings about a shift in wavelength and an angular displacement of optical path.

Solution to Problem

The present invention provides a laser apparatus capable of selecting a wavelength of light to be outputted from a plurality of wavelengths, comprising:
a branching unit which is formed of a polarizer and is configured to branch an optical path formed in a resonator including a reflecting unit having a plurality of fixed reflecting planes and an output mirror, into a plurality of optical paths, thereby forming a common optical path common to the plurality of optical paths which has an end defined by the output mirror and a plurality of different optical path branches respectively corresponding to the plurality of optical paths and each having an end defined by any one of the reflecting planes of the reflecting unit;
a laser medium disposed in the common optical path; and
a selecting unit configured to select, from the plurality of optical path branches, an optical path branch which corresponds to a wavelength of light to be outputted.

The present invention also provides a method of controlling a laser apparatus capable of selecting a wavelength of light to be outputted from a plurality of wavelengths,
the laser apparatus including:
a branching unit configured to branch an optical path formed in a resonator including a reflecting unit having a plurality of fixed reflecting planes and an output mirror, into a plurality of optical paths, thereby forming a common optical path common to the plurality of optical paths which has an end defined by the output mirror and a plurality of different optical path branches respectively corresponding to the plurality of optical paths and each having an end defined by any one of the reflecting planes of the reflecting unit;
a laser medium disposed in the common optical path; and
a polarizer provided on the optical path branches,
the method comprising a selecting step in which a selecting unit selects, from the plurality of optical path branches, an optical path branch which corresponds to a wavelength of light to be outputted.

Advantageous Effects of Invention

According to the present invention, it is possible to provide a laser apparatus having a wavelength selecting system with no mechanically movable structure that brings about a shift in wavelength and an angular displacement of optical path.

Further features of the present invention will become apparent from the following description of exemplary embodiments with reference to the attached drawings.

DESCRIPTION OF EMBODIMENTS

Hereinafter, embodiments of the present invention will be described. It is to be noted that the following description is merely one example for embodying the present invention and, therefore, is not limitative of the scope of the present invention.

(Basic Configuration Using a Prism)

Figure 1:
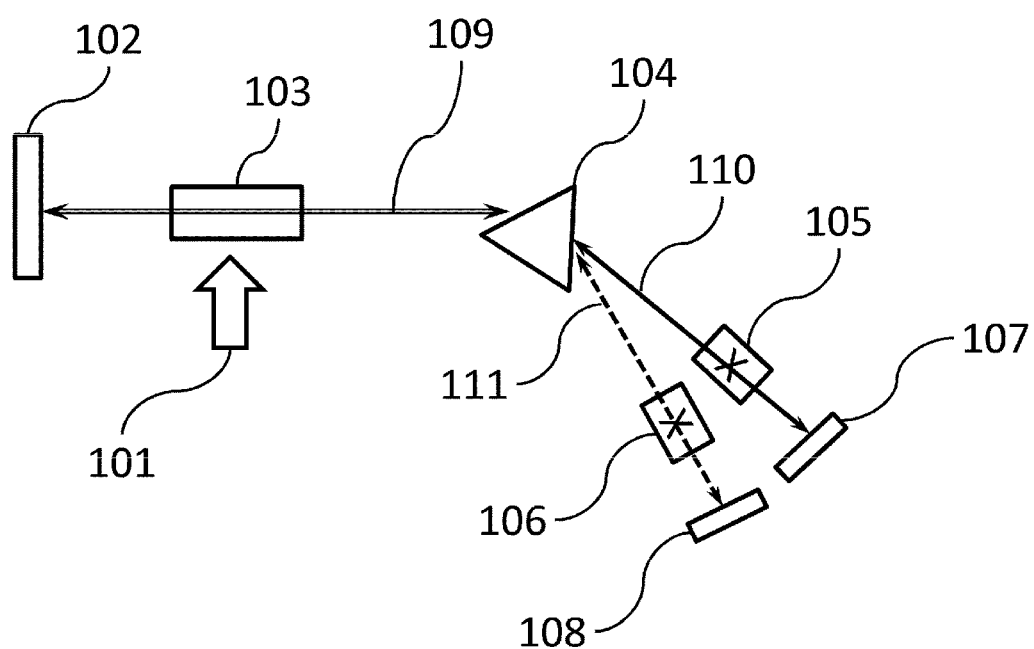
FIG. 1 is a schematic view illustrating one embodiment of a laser apparatus according to the present invention.

FIG. 1 is a schematic view illustrating one embodiment of the present invention.

In FIG. 1 there are included excitation light 101 for exciting a laser medium, an output portion 102, a laser medium 103, a prism 104 serving as an optical path branching portion, and a first optical path shield portion 105 as a resonance optical path selecting portion provided on a first optical path branch 110 which is branched off. In FIG. 1 there is also included a second optical path shield portion 106 as a resonance optical path selecting portion provided on a second optical path branch 111 which is branched off. There are further included a first reflecting member 107 as a reflecting portion provided at an end of the first optical path branch 110, a second reflecting member 108 as a reflecting portion provided at an end of the second optical path branch 111, and a common optical path 109.

The output portion 102 has a dielectric coating stacked thereon which determines a transmittance at an oscillation wavelength in order to generate laser oscillation having a desired wavelength. The laser medium 103 comprises a gain medium having a wide oscillation band, for example, titanium sapphire (Ti:sa), alexandrite, or the like. The prism 104 branches a light beam by chromatic dispersion. The optical material of the prism 104 is preferably a material having a high dispersive power and a high laser damage threshold. The first reflecting member 107 and the second reflecting member 108 are positioned to reflect light of desired wavelengths within the oscillation band of the laser medium 103 and are provided with dielectric coatings suitable for the respective wavelengths.

Laser light excited by a lamp or semiconductor laser, light emitted from a lamp and like light can be used as the excitation light 101 in accordance with applications. For example, in cases where Ti:sa is used as the laser medium, it is often a practice to cause excitation mainly by laser light having a wavelength close to 500 nm. In one preferred form, excitation is caused by using laser light having a wavelength of 532 nm, which is a second harmonic of an Nd:YAG laser. In cases where alexandrite is used as the laser medium, lamp excitation is one preferred form. For a pulse laser to be realized, the excitation light also needs to be pulse-driven. In such a case, it is possible that a flash lamp is used as excitation means and a Q-switch (Q-sw) using a Pockels cell or the like is used in the common optical path 109.

In use, the laser according to the present embodiment is controlled as follows. The following description is directed to an exemplary pulse laser which generates oscillation with a repetition frequency of 20 Hz by the excitation light 101.

For laser light of a first wavelength to oscillate, the first optical path shield portion 105 is opened while the second optical path shield portion 106 closed. The laser medium 103 is excited with the excitation light 101. Laser light of the first wavelength is emitted from a resonator which comprises an optical path consisting of the common optical path 109 and the first optical path branch 110, the output portion 102, and the first reflecting member 107.

After the laser light emission, for laser light of a second wavelength to oscillate, the first optical path shield portion 105 is closed while the second optical path shield portion 106 opened. The opening and closing of the shield portions has to be controlled in view of excitation light triggers, delay time from excitation until oscillation of laser light and a like factor. Preferably, the opening and closing of the shield portions is controlled synchronously with the excitation light triggers. The shield portions can be opened and closed independently. In the present exemplary case, alternate change in oscillation wavelength is made on a pulse-by-pulse basis. A preferred form for ensuring the stability of control of the opening and closing of the shield portions is a rotary type opening and closing system configured to open and close the shield portions repetitively in synchronization with the repetitive frequency, or a like form.

In preparation for the second shot of pulse after completion of control of the shield portions, the laser medium 103 is excited with the excitation light 101 and then laser light of the second wavelength is emitted from a resonator which comprises an optical path consisting of the common optical path 109 and the second optical path branch 111, the output portion 102, and the second reflecting member 108. By repeating this operation, laser light of two wavelengths is allowed to oscillate stably.

In the present embodiment, alternate change in wavelength is made on a pulse-by-pulse basis. However, it is possible that laser light of a desired wavelength is caused to oscillate continuously by selection of a resonator using one of branched light beams by controlling the opening and closing of the shield portions. It is also possible that the order of laser light beams of wavelengths to be oscillated on a pulse-by-pulse basis or the like is preset by programming the control of the opening and closing of the shield portions.

Though the embodiment shown in FIG. 1 uses the single prism 104 as the optical path branching unit, it is difficult for the first optical path branch 110 and the second optical path branch 111 to be separated distinctly when the difference between the oscillation wavelengths is small and, hence, the dispersion is small. A longer resonator length is necessary to separate the optical paths from each other distinctly. In view of this, a plurality of prisms may be used to form the prism 104 so as to widen the optical path branching angle, thereby making it possible to provide a difference between the optical path branches. In this arrangement, the number of prisms to be used is not limited. The two transmitting surfaces of each prism through which an optical path passes may be provided with dielectric anti-reflection coatings with respect to the oscillation wavelength. Alternatively, use may be made of a Brewster dispersion prism which is positioned so that the two transmitting surfaces thereof form a Brewster angle with respect to the wavelength of incident light.

(Arrangement Using a Single Optical Path Shield Portion)

Figure 2:
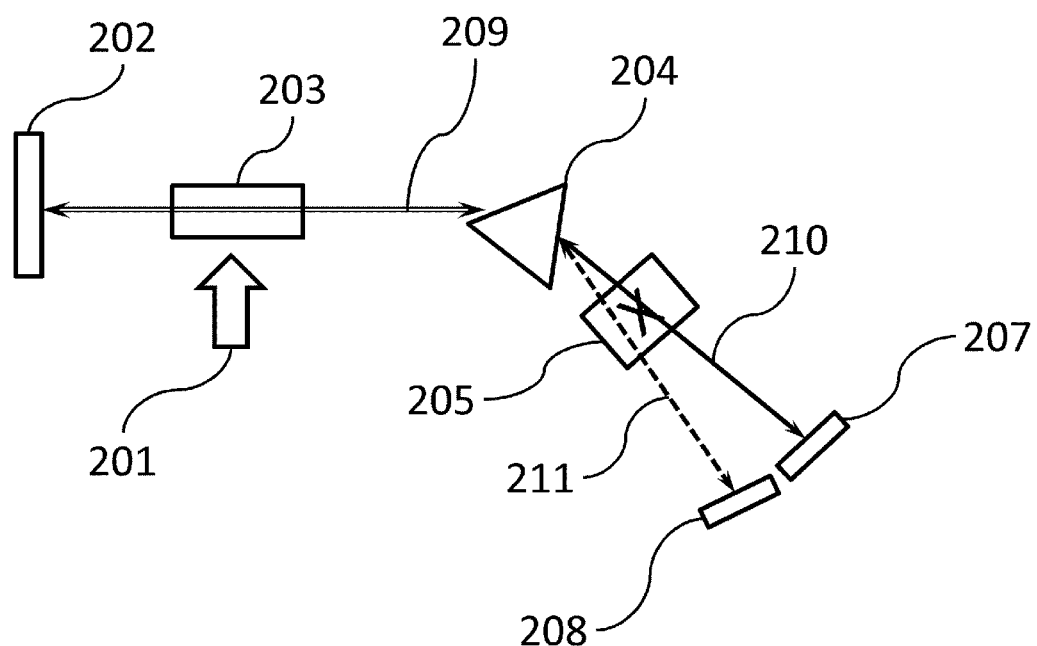
FIG. 2 is a schematic view illustrating one form of an optical path shield portion.

Besides the method in which the optical path branches are provided with the respective optical path shield portions as shown in FIG. 1, an optical path branch selecting method is possible in which a single optical path shield portion 205 stretching over a plurality of optical path branches is provided to shield these optical path branches as shown in FIG. 2. Constitutional elements 201 to 211 other than the optical path shield portion are similar in configuration and function to the elements 101 to 111 shown in FIG. 1. In the case of FIG. 2, optical path selection is possible by using the single shield member which shields one optical path branch while failing to shield the other optical path branch. This method can serve the same purpose as the optical path branch selection using two shield members by changing the optical path to be shielded. Particularly when the difference between the optical path branches is small, the method using the single shield member is effective.

(Arrangement Using a Single Reflecting Member)

Figure 3:
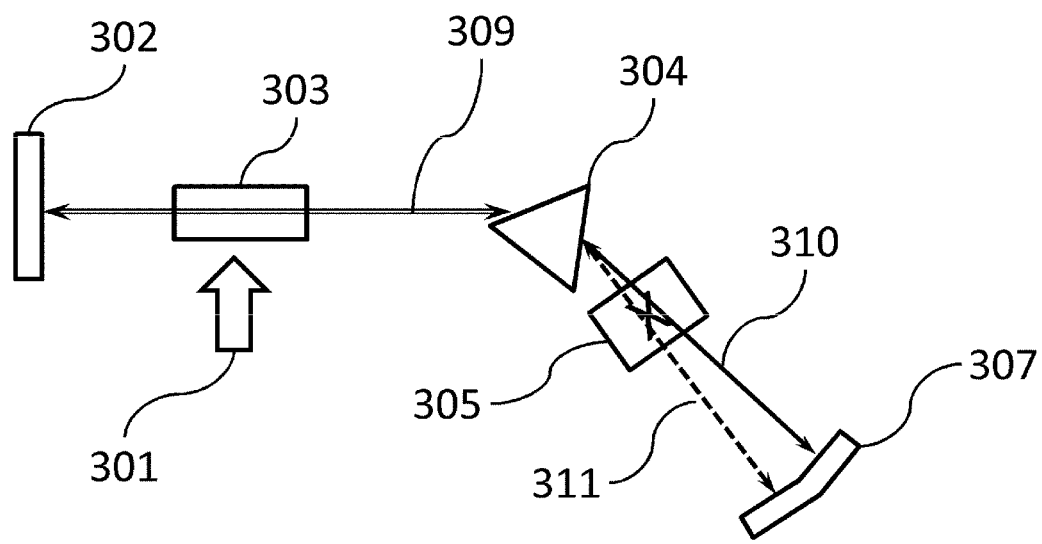
FIG. 3 is a schematic view illustrating one form of a reflecting portion.

In cases where a distinct optical path difference to such an extent as to allow two different reflecting members to be disposed cannot be provided between the first optical path branch and the second optical path branch, it is possible that the reflecting portion is provided with a reflecting member 307 having two reflecting planes which are different in angle from each other as shown in FIG. 3 in order to separate the two optical path branches from each other. In FIG. 3, excitation light 301 for exciting a laser medium, an output portion 302, a laser medium 303, a prism 304 serving as an optical path branching portion and a common optical path 309 are similar in configuration and function to the corresponding elements shown in FIGS. 1 and 2. As in FIG. 2, a single optical path shield portion is provided in this arrangement. The optical path shield portion 305 is disposed so as to stretch over a first optical path branch 310 and a second optical path branch 311 which are branched off by the prism 304, while the reflecting member 307 used to form the reflecting portion of the first optical path branch 310 and that of the second optical path branch 311. In this case, the reflecting member 307 needs to reflect light beams of respective wavelengths to be oscillated correspondingly with angular displacements of optical paths estimated from the refractive index of the prism 304 so that each of the light beams resonates.

(Arrangement Using a Prism as a Reflecting Member)

Figure 4:
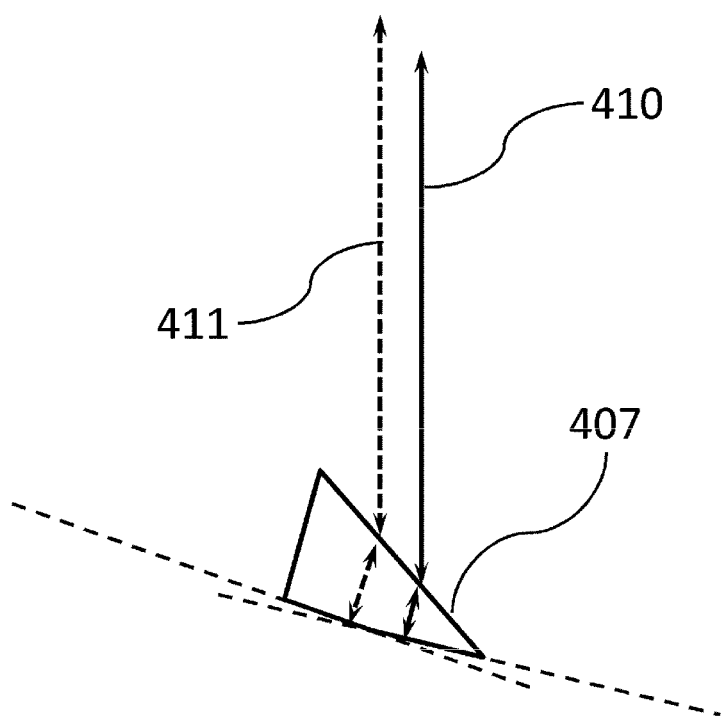
FIG. 4 is a schematic view illustrating a prism used as a reflecting member.

Instead of the reflecting member 307, use may be made of a reflective prism member 407 utilizing internal reflection as shown in FIG. 4. The reflective prism member 407 has a surface in the form of a rectangular equilateral triangle which is positioned so that incident light forms a Brewster angle relative to an incidence plane. Such a reflective prism member is called a "retro-reflecting dispersion prism". Reflecting planes of the reflective prism member 407 are provided with dielectric reflective coatings for respective oscillation wavelengths. In this arrangement, the components forming the resonator are excitation light for exciting a laser medium, an output portion, a laser medium, and a prism serving as an optical path branching portion, as in FIG. 3. In FIG. 4 there are shown a first optical path branch 410 and a second optical path branch 411. Two dotted lines under the prism indicate that the prism has two different reflecting planes. When the reflective prism member has an incidence plane provided with dielectric anti-reflection coatings for the respective wavelengths, the reflective prism member need not be a retro-reflecting dispersion prism.

While each of the arrangements described above relates to a method of branching off light beams of two wavelengths, a wavelength selecting system for selecting two or more wavelengths is possible by increasing the number of reflecting members and the number of reflecting planes of the reflecting member.

(Basic Configuration Using a Parallel Plate)

FIG. 5 is a schematic view illustrating one embodiment of the present invention.

Figure 5A:
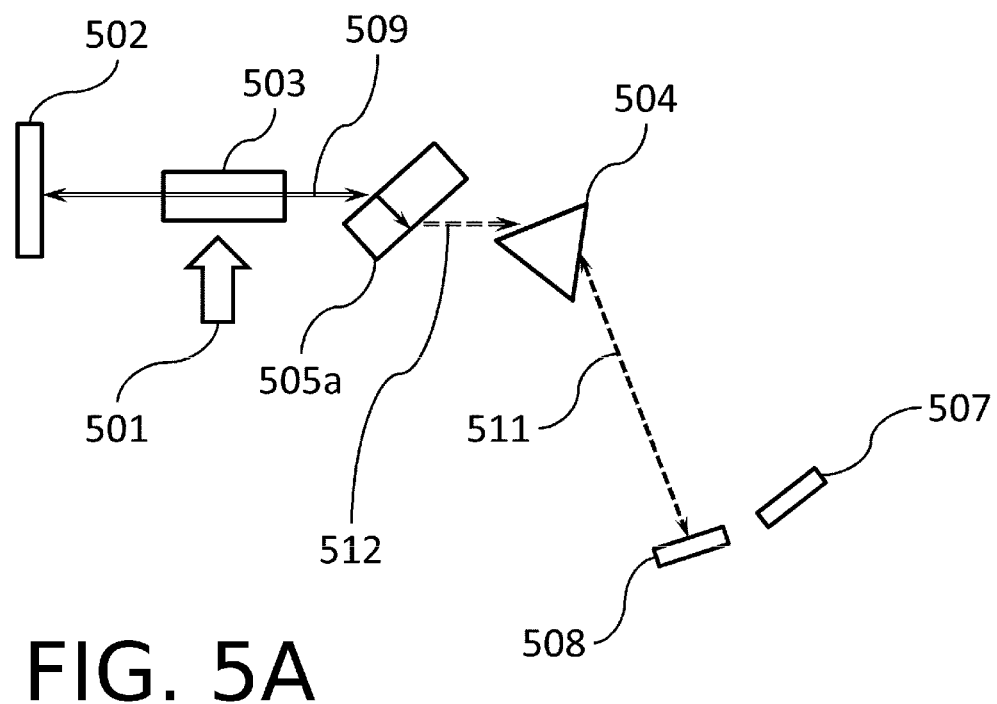
FIGS. 5A and 5B are schematic views illustrating one embodiment of a laser apparatus according to the present invention.
Figure 5B:
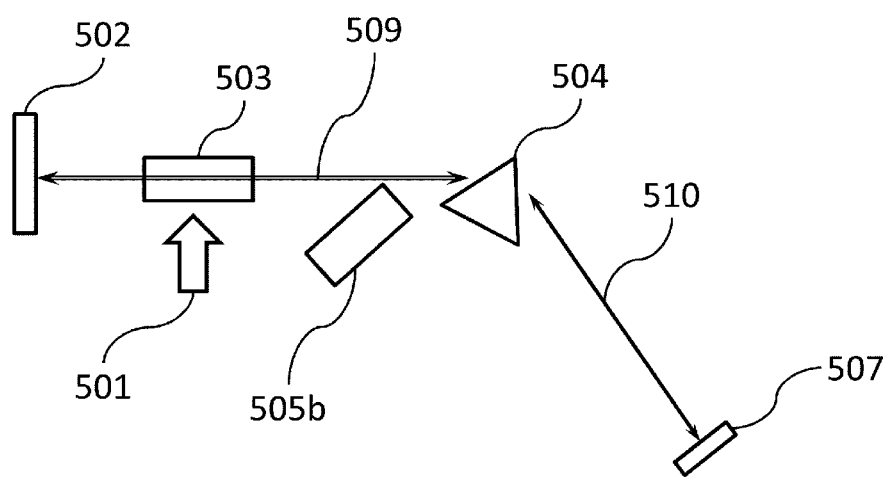

Unlike the embodiment shown in FIG. 1, the embodiment shown in FIG. 5 uses a parallel plate 505 as resonance optical path selecting unit. FIG. 5A illustrates a case where the parallel plate 505 is inserted in an optical path, while FIG. 5B illustrates a case where the parallel plate 505 is not inserted in the optical path. In these cases, different optical path branches are formed. As shown in FIG. 5A, when the parallel plate 505a is inserted in a common optical path 509, a parallel displacement of optical path occurs. That is, the parallel plate is movable between a position on the common optical path and a position out of the common optical path. A resonator is formed which comprises an optical path consisting of the common optical path 509, a parallel-displaced optical path 512 and a second optical path branch 511, an output portion 502 and a second reflecting member 508. As shown in FIG. 5B, on the other hand, when the parallel plate 505b is not inserted in the common optical path 509, a resonator is formed which comprises an optical path consisting of the common optical path 509 and a first optical path branch 510, the output portion 502 and a first reflecting member 507.

The parallel plate 505 preferably comprises a material having a high refractive index and a high laser damage resistance. A preferred one of such materials is quartz. In order to reduce a reflection loss at the parallel plate 505, the parallel plate 505 in the position on the common optical path is preferably oriented to form a Brewster angle relative to incident light. In one preferred form, however, the light-incidence plane and light-outgoing plane of the parallel plate are both provided with respective dielectric anti-reflection coatings.

A laser apparatus capable of two-wavelength oscillation is realized by establishing the positions of the respective reflecting members to cause resonances with desired wavelengths to occur and moving the parallel plate 505 by control on a pulse-by-pulse basis. Though the movement of the parallel plate may be linearly driven, one preferred form for more stabilized control is rotary driving to switch the parallel plate between the position on the common optical path 509 and the position out of the common optical path 509 by rotating the parallel plate without changing the positions of light-incidence and light-outgoing planes of the parallel plate.

Though the drive member is inserted into the resonance optical path according to the present embodiment, there is a low possibility of an angular displacement of optical path when a slight displacement of the drive member occurs because the optical path is merely moved parallel. Thus, a stabilized resonant state can be maintained.

(Arrangement Using Two Parallel Plates)

Figure 6:
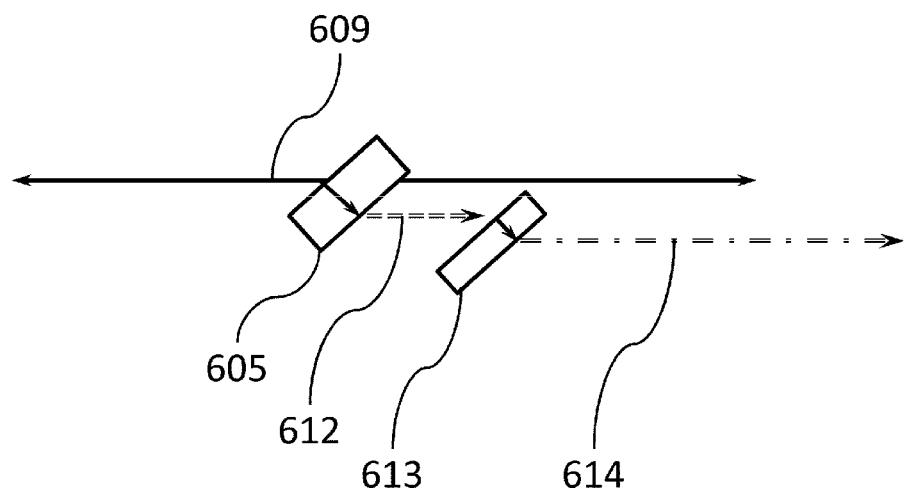
FIG. 6 is a schematic view illustrating an optical path selecting system using parallel plates.

In order to increase a parallel displacement of optical path, a movable parallel plate 605 and a fixed parallel plate 613 as shown in FIG. 6 may be used instead of the parallel plate 505 shown in FIG. 5. Specifically, the fixed parallel plate is disposed on a first parallel-displaced optical path 612 which is formed when the movable parallel plate 605 is inserted into the common optical path, thereby forming a second parallel-displaced optical path 614 which is parallel-displaced more largely.

Though it is possible to increase the parallel displacement by increasing the thickness of the movable parallel plate, this arrangement has a drawback such that the weight of the movable member increases. In view of this, by dividing the parallel plate into two as shown in FIG. 6, the amount of parallel displacement can be increased without increasing the weight of the movable parallel plate.

(Arrangement Using a Wedge-Shaped Optical Member)

Figure 7:
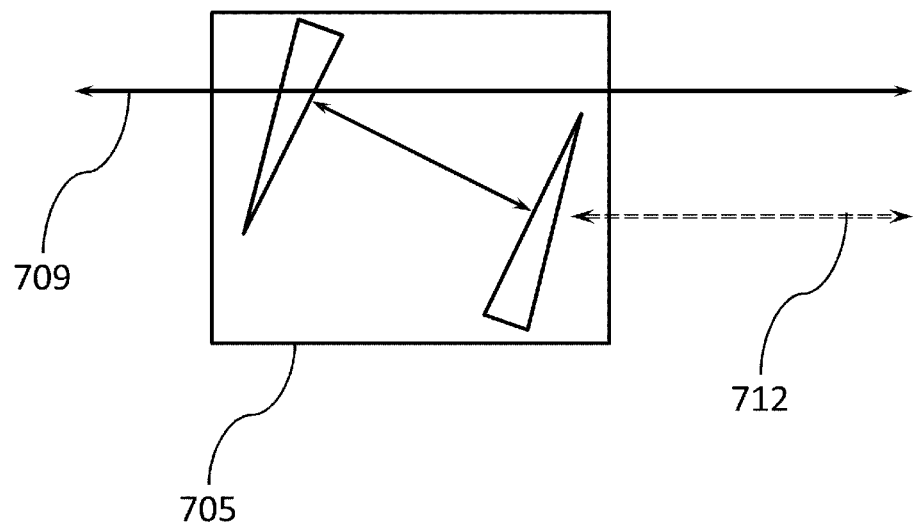
FIG. 7 is a schematic view illustrating an optical path selecting system using wedge-shaped elements.

As shown in FIG. 7, a wedge-shaped optical member pair 705 comprising two wedge-shaped optical members as a pair may be used instead of the parallel plate 505. The wedge-shaped optical member pair 705 is inserted between a common optical path 709 and a parallel-displaced optical path 712. The use of this member makes it possible to provide a distinct optical path difference.

(Arrangement for Separating Three or More Wavelengths Using a Parallel Plate)

Figure 14:
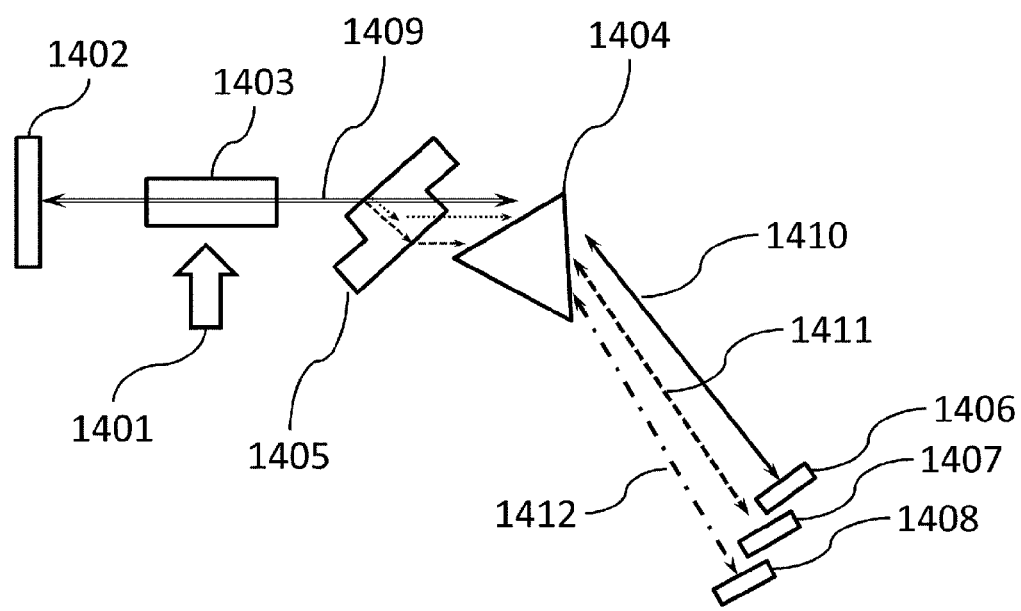
FIG. 14 is a schematic view illustrating one embodiment of a laser apparatus according to the present invention.

The method of providing an optical path difference between optical path branches with use of a parallel plate is capable of more easily separating optical paths from each other than the method using only the prism 104 shown in FIG. 1. Therefore, the method using the parallel plate can easily provide for a laser capable of selecting three or more oscillation wavelengths. FIG. 14 illustrates a laser which selects three wavelengths using a parallel plate.

In FIG. 14 there are included excitation light 1401 for exciting a laser medium, an output portion 1402, a laser medium 1403, a prism 1404 serving as an optical path branching portion, a first optical path branch 1410, a second optical path branch 1411, and a third optical path branch 1412. In FIG. 14 there are also included a first reflecting member 1406, a second reflecting member 1407 and a third reflecting member 1408 which form reflecting portions of the respective optical path branches, and a common optical path 1409.

A parallel plate 1405 having portions which are different in thickness from each other is provided by bonding parallel plates by optical contact. The parallel plate 1405 having different thicknesses is inserted into the common optical path 1409. By changing the insert position of the parallel plate 1405, the length of an optical path passing through the parallel plate is changed because the thickness of the parallel plate changes with changing insert position, whereby the amount of optical path displacement also changes. In this way, it is possible to form resonator structures corresponding to the three optical path branches, thereby to form a laser apparatus capable of three-wavelength oscillation. Though the parallel plate formed by bonding by optical contact is illustrated here, it is possible to form a laser capable of multiple-wavelength oscillation by providing multiple stages of optical path displacement by means of a plurality of parallel plates positioned parallel with each other as shown in FIG. 6.

(Arrangement Using a Branching Polarizer and a Resonance Optical Path Selecting Portion)

The embodiments described above, which use a prism as an optical path branching portion, each need means for separating the positions of fixed reflecting portions corresponding to respective wavelengths by at least the size or shape of each beam having respective wavelength in order to reduce the resonator size. The following embodiment is a more preferable embodiment which is capable of distinct optical path separation without increasing the number of optical members to be used.

Figure 8:
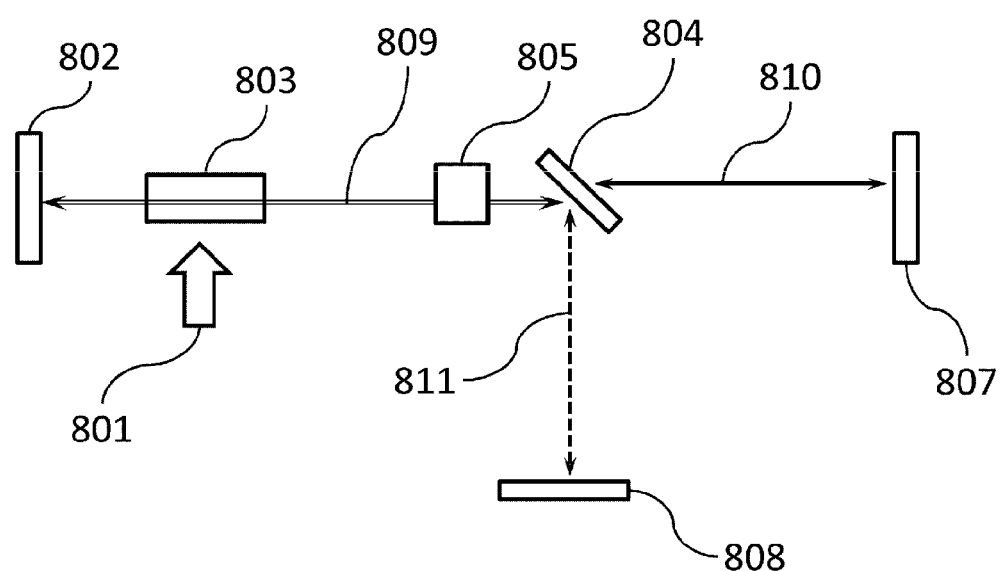
FIG. 8 is a schematic view illustrating one embodiment of a laser apparatus according to the present invention.

FIG. 8 is a schematic view illustrating one embodiment of the present invention.

In FIG. 8 there are included excitation light 801 for exciting a laser medium, an output portion 802, a laser medium 803, a branching polarizer 804 serving as an optical path branching portion, and a polarization rotating member as a resonance optical path selecting portion 805. The polarization rotating member as the resonance optical path selecting portion is a Pockels cell or a Faraday rotator for example. In FIG. 8 there are also included a first reflecting member 807 as a reflecting portion of a first optical path branch 810, a second reflecting member 808 as a reflecting portion of a second optical path branch 811, and a common optical path 809.

The first reflecting member 807 and the second reflecting member 808 reflect respective of desired wavelengths within the oscillation band of the laser medium 803 to form resonators having respective of the first optical path branch 810 and the second optical path branch 811 as their optical paths. The reflecting members are each provided with a respective one of dielectric reflective coatings which reflect light of desired wavelengths. Since light of wavelengths other than light of the wavelengths reflected by the dielectric reflective coatings incurs too much loss in the resonator to generate laser oscillation, the oscillation wavelength is fixed. Therefore, a laser oscillator which reflects light with two desired wavelength ranges can be formed by differentiating the wavelength ranges of light reflected by the dielectric reflective coatings provided on the respective reflecting members 807 and 808.

The wavelength width of the oscillating laser depends on the characteristics of the dielectric reflective coating provided on each reflecting member, unlike the embodiment shown in FIG. 1 which uses a prism as the optical path branching portion. Therefore, oscillation with a narrow-band wavelength of not more than several nm is difficult. Easy methods which enable narrow-band oscillation to be generated include a method using retro-reflecting dispersion prisms as shown in FIG. 4 as the reflecting members instead of the plate members provided with the dielectric reflective coatings as shown in FIG. 8. Narrowing the bandwidth is possible by using reflective prism members on the respective optical path branches in such a manner as to reflect and resonate light of desired wavelengths matched with dispersions by the retro-reflecting dispersion prisms.

The branching polarizer 804 comprises a plate-type polarizing beam splitter or the like. The branching polarizer 804 has an incidence plane on the side on which a light beam from the common optical path 809 is incident and a reflecting plane which is opposite away from the incidence plane, the incidence plane being provided with a dielectric coating which selects transmission or reflection depending on the polarization of incident light, the reflecting plane being provided with a dielectric anti-reflection coating which transmits an incident light beam.

The following description is directed to the case where the Pockels cell is used as the resonance optical path selecting portion 805. There is no particular limitation as long as the present embodiment has a system for 90°-polarizing the polarized states of incident light and reflected light. Therefore, the arrangement remains the same even when the Faraday rotator is used. In the present embodiment, the resonance optical path selecting portion is controlled during pulse oscillation intervals.

When the optical path to be used comprises the common optical path 809 and the first optical path branch 810, a resonator comprising the output portion 802 and the first reflecting member 807 generates laser oscillation of a first wavelength. When the optical path to be used comprises the common optical path 809 and the second optical path branch 811, a resonator comprising the output portion 802 and the second reflecting member 808 generates laser oscillation of a second wavelength. Optical path selection can be made by shifting the phase of transmitted light by 90° relative to the phase of incident light by application of high voltage to the Pockels cell 805, thereby changing the resonator to generate laser oscillation. When linear polarization of incident light is p-polarization for example, the polarization of transmitted light is maintained as p-polarization by turning OFF the applied voltage. As a result, the p-polarized light passes through the branching polarizer 804 to generate oscillation of laser light of the first wavelength. When the linear polarization of incident light is rotated 90° by turning ON the applied voltage to obtain transmitted light of s-polarization, the s-polarized light is reflected by the branching polarizer 804 to generate oscillation of laser light of the second wavelength using the second optical path branch. The use of the Pockels cell as the resonance optical path selecting portion realizes a wavelength selecting system having no mechanically movable portion.

In use, the laser according to the present embodiment is controlled as follows. The following description is directed to an exemplary pulse laser which generates oscillation with a repetitive frequency of 20 Hz by using the excitation light 801.

The polarization direction of light in the common optical path 809 depends on the excitation method, laser medium and the like. For example, in a Ti:sa laser using a second harmonic of an Nd:YAG laser as excitation light, the polarization direction of the excitation light is the polarization direction of Ti:sa. In the case of Ti:sa, the excitation light absorption characteristics thereof depend on the polarization and, hence, a Ti:sa crystal is positioned so as to absorb the excitation light intensively, thereby obtaining desired linearly polarized light. In the case of flash lamp excitation, when the laser medium has uniaxial anisotropy, oscillation is generated in a polarization direction in which the laser medium exhibits a high absorption coefficient and, hence, the laser medium is positioned so as to generate oscillation with a desired polarization. In one preferred form, a polarizer is disposed between the laser medium 803 and the Pockels cell 805 so as to allow only desired linearly polarized light to pass therethrough.

Applied voltage switching of the Pockels cell is performed within 50 ms for which oscillation of a first pulse and a second pulse is generated. In order to shorten the time taken for voltage application, voltage application is maintained only during a time period associated with oscillation. Specifically, in the case of laser excitation, voltage application is started before the excitation light 801 becomes incident on the laser medium 803 and stopped after completion of laser oscillation by resonance. In the case of a laser which generates pulse oscillation by a Q-switch (Q-sw) using flash lamp excitation, the Q-value of the resonator is raised by the Q-sw and then application of voltage to the Pockels cell forming the resonance optical path selecting portion is turned ON before the generation of pulse oscillation. After completion of laser oscillation following the occurrence of resonance, the voltage application is stopped.

Oscillation with a desired wavelength is possible by electrically controlling the polarized state by the resonance optical path selecting portion synchronously with each pulse.
(Arrangement Using a Branching Polarizer, a Resonance Optical Path Selecting Portion, and a Shield Member)

Figure 9:
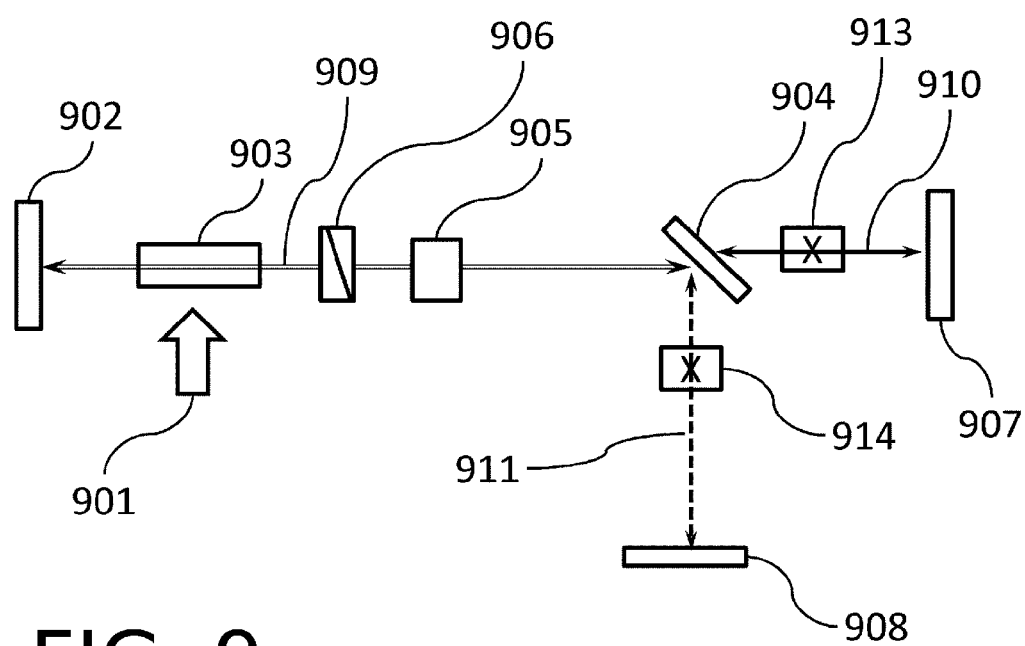
FIG. 9 is a schematic view illustrating one embodiment of a laser apparatus according to the present invention.

FIG. 9 is a schematic view illustrating one embodiment of the present invention.

In FIG. 9 there are included excitation light 901 for exciting a laser medium, an output portion 902, a laser medium 903, a branching polarizer 904 serving as an optical path branching portion, and a Pockels cell 905 serving as a resonance optical path selecting portion and a Q-switch (Q-sw) both. In FIG. 9 there are also included a first polarizer 906 as a Q-sw forming member, a first reflecting member 907 as a reflecting portion of a first optical path branch 910, and a second reflecting member 908 as a reflecting portion of a second optical path branch 911. In FIG. 9 there are further included a first shield member 913 as a shield portion of the first optical path branch 910, a second shield member 914 as a shield portion of the second optical path branch 911, and a common optical path 909.

Unlike the embodiment shown in FIG. 8, the present embodiment has an arrangement in which the Pockels cell 905 serves as the Q-switch (Q-sw) for generating giant pulse oscillation and the Q-sw drive also plays the role of the resonance optical path selecting portion. Q-sw systems include a system for a λ/4 polarization change by application of voltage to the Pockels cell and a system for a λ/2 polarization change by application of voltage to the Pockels cell. The present embodiment uses the Q-sw for the λ/2 polarization control system. The Q-sw comprises the first polarizer 906 and the Pockels cell 905. The polarization direction of the first polarizer 906 is the polarization direction of light passing through the branching polarizer 904. In the present embodiment, p-polarized light is allowed to pass through the branching polarizer 904.

As in the embodiment shown in FIG. 8, there are two possible cases where: the reflecting members 907 and 908 each having a narrow-band dielectric reflective coating are used for oscillation wavelength selection; and the reflecting members 907 and 908 each comprising a reflective prism member are used for oscillation wavelength selection.

In use, the laser according to the present embodiment is controlled as follows. The following description is directed to an exemplary pulse laser which generates oscillation with a repetitive frequency of 20 Hz by using excitation light.

In generating laser oscillation of a first wavelength by using a first pulse and a resonator having an optical path comprising the common optical path 909 and the optical path branch 910, a process 1 described below is carried out.

(Process 1) The first optical path shield portion 913 is opened and the second optical path shield portion 914 closed. Voltage is applied to the Pockels cell 905 before the flash lamp irradiates the laser medium 903 with the excitation light 901. Spontaneous emission light from the laser medium partially passes through the first polarizer 906. The polarization direction of transmitted light is p-polarization. A light beam having passed through the Pockels cell is linearly polarized light of s-polarization by 90° rotation of polarization direction. The light beam is reflected by the branching polarizer 904, but cannot pass through the second shield member 914 in the closed state. This state is maintained until the population inversion density of the laser medium 903 reaches a high level. At the time the emission output is maximized, the voltage applied to the Pockels cell is turned OFF. As a result, the light beam passing through the Pockels cell 905 remains as p-polarized light and passes through the branching polarizer 904, so that the Q-value of the resonator having an optical path comprising the common optical path 909 and the optical path branch 910 rises to cause laser oscillation to be generated. That is, laser oscillation is generated by turning OFF the applied voltage.

In generating oscillation of the first wavelength by using a second pulse, the process 1 described above is repeatedly carried out. In generating oscillation of a second wavelength by using the second pulse, a process 2 described below is carried out.

(Process 2) The first optical path shield portion 913 is closed and the second optical path shield portion 914 opened. The application of voltage to the Pockels cell 905 is OFF after the first pulse oscillation. The flash lamp irradiates the laser medium 903 with the excitation light 901. Spontaneous emission light from the laser medium partially passes through the first polarizer 906. The polarization direction of transmitted light is p-polarization. The polarization direction of a light beam having passed through the Pockels cell is maintained as it is. The light beam passes through the branching polarizer 904, but cannot pass through the first shield member 913 in the closed state. This state is maintained until the population inversion density of the laser medium 903 reaches a high level. At the time the emission output is maximized, voltage is applied to the Pockels cell. As a result, the light beam passing through the Pockels cell 905 is changed into s-polarized light and is reflected by the branching polarizer 904, so that the Q-value of the resonator having an optical path comprising the common optical path 909 and the optical path branch 911 rises to cause laser oscillation to be generated. That is, laser oscillation is generated by turning ON the application of voltage. The ON-state is maintained until completion of the laser oscillation. The linear polarization of the light beam reflected by the reflecting member 908 is maintained as s-polarization and the light beam is reflected by the polarizer 904 again. Since the voltage applied to the Pockels cell is in ON-state, the beam becomes p-polarized light after having passed through the Pockels cell and hence can pass through the first polarizer, thus forming a resonator having a high Q-value.

In generating oscillation of the second wavelength by using the second pulse, the process 2 described above is repeatedly carried out. In generating oscillation of the first wavelength by using a third pulse, the process 1 is carried out again.

The driver used to drive the Pockels cell 905 in the process 1 for generating oscillation when the voltage is OFF is different from that used to drive the Pockels cell 905 in the process 2 for generating oscillation when the voltage is ON. Particularly in the process 2, the voltage ON-state need be such that: a rise in applied voltage is steep; the population inversion energy accumulated in the laser medium is converted to a laser light output; and the ON-state is maintained until completion of laser oscillation. An electric circuit makes a selection such as to change the driver to be used according to the wavelength selection.

As described with reference to the foregoing arrangements, a PAT apparatus incorporating the laser oscillator according to the present invention is capable of irradiating a living body with stably oscillating laser beams of two or more wavelengths selectively without the need to take a wavelength shift and an optical path displacement into consideration for a long term. Particularly, by determining the oxidized state of hemoglobin present in blood, functional information from inside a living body which originates from blood can be extracted. Because the absorption coefficient of oxidized hemoglobin and that of reduced hemoglobin cross each other at about 800 nm, a PAT apparatus using a wavelength range about 800 nm is capable of determining the condition of the blood.

The use of the laser apparatus according to the present invention enables irradiation with laser light of a desired wavelength on a laser pulse-by-laser pulse basis to be performed as required, thereby providing for a PAT apparatus having the following features.

A fixed type PAT apparatus has been devised which is configured to scan a PAT probe over a fixed living body, the PAT probe having an ultrasound element and a laser beam emitting portion which are integrated with each other. By switching between oscillation wavelengths on a pulse-by-pulse basis, photoacoustic waves based on irradiation light beams having different wavelengths can be obtained from substantially the same position even when the scanning speed of the PAT probe is increased, thereby making rapid diagnosis possible. Further, since photoacoustic waves based on irradiation light beams having different wavelengths can be obtained from substantially the same part at substantially the same time, the effect by displacement of the location of measurement or the like due to breathing or the like can be reduced. That is, it is possible to compare received signals resulting from irradiation light beams of two wavelengths to each other with high precision.

A handheld type PAT apparatus has been also devised which is made by imparting a conventional ultrasonograph with a photoacoustic wave acquiring function. In the case of such a handheld apparatus, a medical service worker using the handheld apparatus operates a PAT probe for scanning at a desired place with desired timing. Like the fixed type PAT apparatus described above, the handheld type PAT apparatus can be handled without taking an oscillation wavelength to be used into consideration because the oscillation wavelength changes on a pulse-by-pulse basis and hence is very useful.

With the PAT apparatus incorporating the laser apparatus according to the present invention which exhibits high oscillation stability to wavelength selection, destabilization need not be taken into consideration even when the repetitive frequency becomes higher and, hence, stabilized oscillation on a pulse-by-pulse basis is possible.

Even in the case where wavelength switching is made every several pulses or every several ten pulses, the PAT apparatus has no problem with oscillation stability and hence can find various uses. In particular, the embodiment shown in FIG. 8 which uses polarized light can perform wavelength switching only by electrical signals and hence can be readily adapted to a usage in which oscillation wavelengths are previously programmed. For this reason, the laser apparatus has wide applicability to various usages of the PAT apparatus.

In the foregoing arrangements, the optical path branching portion is equivalent to the "branching unit" according to the present invention. The resonance optical path selecting portion is equivalent to the "selecting unit" according to the present invention. The reflecting portion is equivalent to the "reflecting unit" according to the present invention. The optical path shield portion is equivalent to the "shield member" according to the present invention. The dielectric anti-reflection coating is equivalent to the "anti-reflection coating" according to the present invention. The dielectric reflective coating is equivalent to the "reflective coating" according to the present invention.

Embodiment 1

One embodiment of a laser apparatus for use in a medical photoacoustic tomography apparatus (medical PAT apparatus) is described below.

Figure 10:
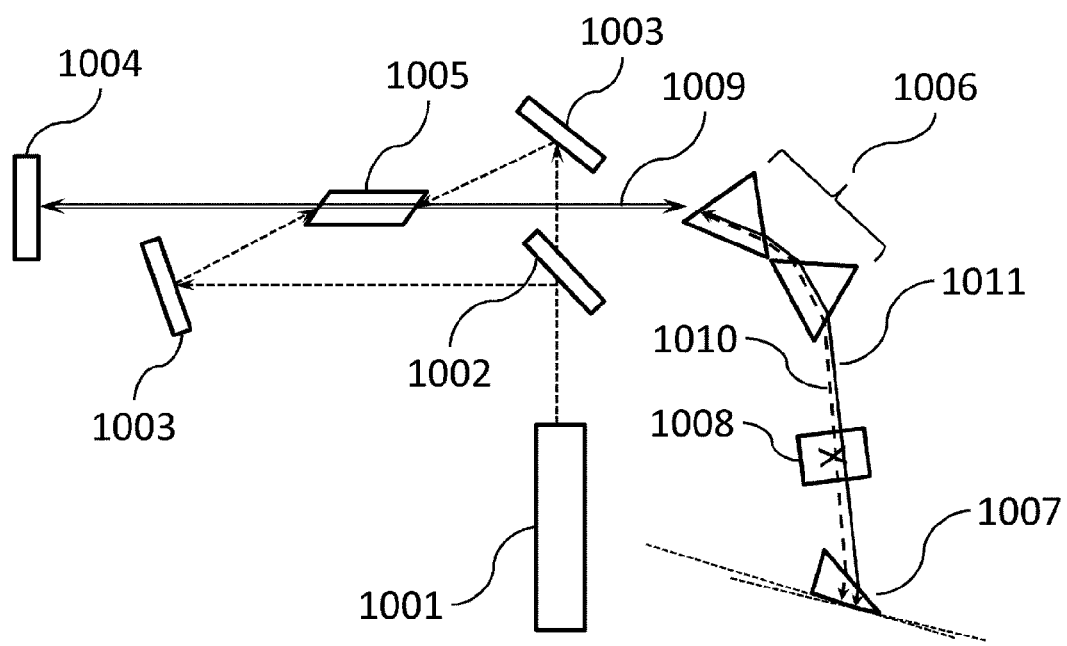
FIG. 10 is a schematic view of embodiment 1.

FIG. 10 is a schematic view illustrating a laser apparatus incorporated in the medical PAT apparatus. This laser apparatus is a titanium sapphire laser using a second harmonic of an Nd:YAG laser as an excitation source and is capable of generating laser oscillation with wavelengths of 850 nm and 700 nm. The laser apparatus is driven by excitation light at a repetitive frequency of 10 Hz. The output power is 100 mJ/pulse. The titanium sapphire laser has the following configuration. An excitation section includes an excitation light source 1001 configured to generate the second harmonic of the Nd:YAG laser, an excitation light beam splitter 1002, and an excitation light reflecting member 1003. The titanium sapphire laser has a resonance section comprising an output mirror 1004, a titanium sapphire crystal 1005 as a laser medium, a branching prism 1006 as an optical path branching portion, an optical path shield portion 1008 as a resonance optical path selecting portion, and a reflective prism 1007 as a reflecting member. The optical path branching portion (branching prism 1006) comprises two prisms. The resonance optical path selecting portion (optical path shield portion 1008) is disposed on optical path branches which are branched off. The reflecting member (reflective prism 1007) is a reflective prism having two reflecting planes which reflect light beams having respective wavelengths of 850 nm and 700 nm to allow resonance to occur.

The laser apparatus has optical paths including a first optical path branch 1010 serving as a resonance optical path for laser light of 700 nm, a second optical path branch 1011 serving as a resonance optical path for laser light having a wavelength of 850 nm, and a common optical path 1009. The common optical path 1009 has a length of not more than 300 mm, and the spacing between the reflective prism 1007 and the closer one of the prisms forming the branching prism 1006 is set to 112 mm. Though there is no particular limitation on the resonator size, the present embodiment uses an illustrative resonator size which allows the two optical path branches to be separated from each other and is not too large.

The excitation light has p-polarization relative to the incidence plane of the titanium sapphire crystal. The oscillation of the titanium sapphire laser maintains p-polarization also. The branching prism 1006 is a Brewster dispersion prism of quarts having a vertical angle of 69.07° which is positioned so that its 800-nm wavelength incidence plane forms a Brewster angle relative to incident light. By using two such prisms, a certain difference in angle is provided between the optical path for light having an oscillation wavelength of 700 nm and that for light having an oscillation wavelength of 850 nm. The reflective prism 1007 is a retro-reflecting dispersion prism which has a vertical angle ½ as large as the vertical angle of the branching prism and which is positioned so that its incidence plane forms an angle close to the Brewster angle relative to incident light. The reflective prism has different reflecting planes for the first optical path branch 1010 and the second optical path branch 1011 as shown in FIG. 10 which reflect light of 850-nm wavelength and light of 700-nm wavelength to form respective resonators. The reflecting planes are provided with dielectric reflective coatings for the respective wavelengths.

The optical path shield means 1008 is a shutter capable of shielding the optical path branches alternately and independently.

Using the laser apparatus described above with a first pulse at 700 nm and a second pulse at 850 nm, laser oscillation was generated with alternate change in wavelength on a pulse-by-pulse basis. Before the first pulse oscillation, the second optical path branch 1011 was shielded. The titanium sapphire was excited by excitation light of 532-nm wavelength oscillated by the excitation source 1001. Light thus generated was allowed to resonate in an optical path passing through the first optical path branch 1010 and then emitted as laser light having a wavelength of 700 nm from the output mirror 1004. After the first pulse oscillation, the optical path shield portion 1008 switched the shutter to shield the first optical path branch 1010. Thereafter, the titanium sapphire was irradiated with excitation light for the second pulse from the excitation source 1001. Light thus generated was allowed to resonate in an optical path passing through the second optical path branch 1011 and then emitted as laser light having a wavelength of 850 nm from the output mirror 1004.

The output light beams thus obtained were measured for their wavelengths and energy on a pulse-by-pulse basis. Light having a wavelength of 700 nm and light having a wavelength of 850 nm were alternately emitted, and the energy stability of each pulse was substantially the same as that of the second harmonic serving as the excitation light. Thus, very stable oscillation was obtained.

The present laser has no mechanically movable structure in a system associated with wavelength change, particularly in the optical paths of the resonators for oscillation and hence is excellent in long-term stability and has a very low possibility that misalignment or the like occurs. The laser is constructed using optical components each having a high energy damage threshold and incurs a small optical energy loss at each optical component inside the resonator. Therefore, high irradiation energy was obtained as an output energy of 100 mJ/pulse.

The present laser apparatus was incorporated in a fixed type PAT apparatus configured to scan a PAT probe over a part of a fixed living body, the PAT probe having an ultrasound element and a laser beam emitting portion which were integrated with each other. A relatively wide measurement range of a living body imitation sample was scanned with a repetitive frequency of 20 Hz. In the measurement, switching was made between 700-nm wavelength and 850-nm wavelength on a pulse-by-pulse basis to acquire functional information characteristic of each wavelength. As a result, the use of the laser apparatus according to the present invention made it possible to acquire highly precise functional information with a little effect on received signals by a position displacement and a measurement time lag.

Embodiment 2

One embodiment of a laser apparatus for use in a medical photoacoustic tomography apparatus (medical PAT apparatus) is described below.

Figure 11:
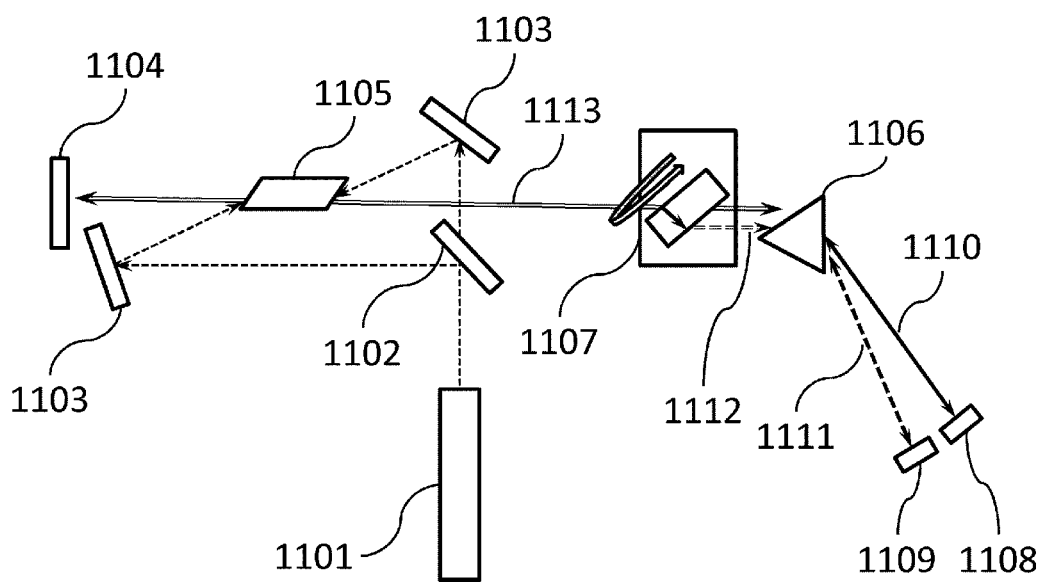
FIG. 11 is a schematic view of embodiment 2.

FIG. 11 is a schematic view illustrating a laser apparatus incorporated in the medical PAT apparatus. This laser apparatus is a titanium sapphire laser using a second harmonic of an Nd:YAG laser as an excitation source and is capable of generating laser oscillation with wavelengths of 800 nm and 755 nm. The laser apparatus is driven by excitation light at a repetitive frequency of 20 Hz. The output power is 120 mJ/pulse. The titanium sapphire laser has the following configuration. An excitation section includes an excitation light source 1101 configured to generate a second harmonic of the Nd:YAG laser, an excitation light beam splitter 1102, and an excitation light reflecting member 1103. The titanium sapphire laser has a resonance section comprising an output mirror 1104, a titanium sapphire crystal 1105 as a laser medium, a branching prism 1106 as an optical path branching portion, and a parallel plate 1107 as an optical path branching portion. A reflecting member comprises a first reflecting plate 1108 which reflects a light beam having a wavelength of 800 nm, and a second reflecting plate 1109 which reflects a light beam having a wavelength of 755 nm. The laser apparatus has optical paths including a first optical path branch 1110 serving as a resonance optical path for laser light of 800 nm, a second optical path branch 1111 serving as a resonance optical path for laser light having a wavelength of 755 nm, a common optical path 1113, and a parallel-displaced optical path 1112 formed by the parallel plate.

The excitation light has p-polarization relative to the incidence plane of the titanium sapphire crystal. The oscillation of the titanium sapphire laser maintains p-polarization also. The parallel plate 1107 is positioned so that its incidence plane forms a Brewster angle relative to incident light, thereby minimizing an energy loss by reflection. The reflecting planes of the first and second reflecting members 1108 and 1109 are provided with dielectric anti-reflection coatings for reflecting light beams having the respective wavelengths of 755 nm and 800 nm. The difference in reflection angle between the two reflecting planes is about 0.1°.

Quartz having a thickness of 20 mm was used as the parallel plate 1107. The parallel plate has a shape such that a portion forming an incidence and reflection plane is circularly cut out partially. The parallel plate has an axis of rotation perpendicular to the incidence and reflection plane. The axis of rotation is positioned out of the common optical path 1113. Rotary driving of such a parallel plate can stably bring about a state in which the parallel plate 1107 is inserted in the optical path and a state in which the parallel plate 1107 is not inserted in the optical path. The parallel plate 1107 is inserted into the common optical path 1113 to form the parallel-displaced optical path 1112 when 800-nm wavelength oscillation is to be generated. When 755-nm wavelength oscillation is to be generated, the parallel plate 1107 is not inserted into common optical path 1113.

A Brewster dispersion prism having vertical angle of 69.07° was used as the branching prism 1106 and was positioned so as to have an incidence plane forming a Brewster angle relative to incident light having a wavelength of 800 nm.

Using the laser apparatus described above with a first pulse at 800 nm and a second pulse at 755 nm, laser oscillation was generated with alternate change in wavelength on a pulse-by-pulse basis. Before the first pulse oscillation, the parallel plate 1107 was inserted into the common optical path 1113. The titanium sapphire was excited by excitation light of 532-nm wavelength oscillated by the excitation source 1101. Light thus generated was allowed to resonate in an optical path passing through the first optical path branch 1110 and then emitted as laser light having a wavelength of 800 nm from the output mirror 1104. After the first pulse oscillation, the parallel plate 1107 was withdrawn from the common optical path 1113. Thereafter, the titanium sapphire was irradiated with excitation light for the second pulse from the excitation source 1101. Light thus generated was allowed to resonate in an optical path passing through the second optical path branch 1111 and then emitted as laser light having a wavelength of 755 nm from the output mirror 1104.

The output light beams thus obtained were measured for their wavelengths and energy on a pulse-by-pulse basis. Light having a wavelength of 800 nm and light having a wavelength of 755 nm were alternately emitted, and the energy stability of each pulse was substantially the same as that of the second harmonic serving as the excitation light. Thus, very stable oscillation was obtained.

The present laser has no driving component that brings about an optical path displacement such as to impede resonance. Though the parallel plate is movable, the parallel plate is stably rotary-driven. Each wavelength always has a fixed direction since no angular displacement of the associated optical path takes place and, hence, wavelength reproducibility is very high. As a result, the present laser is excellent in long-term stability with a very low possibility that an energy drop or a like problem arises due to misalignment or the like. The laser is constructed using optical components each having a high energy damage threshold and incurs a small optical energy loss at each optical component inside the resonator. Therefore, high irradiation energy was obtained as an output energy of 120 mJ/pulse.

The present laser apparatus was incorporated in a fixed type PAT apparatus configured to scan a PAT probe over a part of a fixed living body, the PAT probe having an ultrasound element and a laser beam emitting portion which were integrated with each other. A measurement sample used was a living body imitation sample having a blood vessel in which oxidized type hemoglobin limitation and reduced type hemoglobin imitation were present. The sample was scanned with a repetitive frequency of 20 Hz. In the measurement, switching was made between 700-nm wavelength and 850-nm wavelength on a pulse-by-pulse basis to acquire functional information characteristic of each wavelength. The use of the laser apparatus according to the present invention made it possible to acquire highly precise functional information with a little effect on received signals by a position displacement or a measurement time lag.

Embodiment 3

One embodiment of a laser apparatus for use in a medical photoacoustic tomography apparatus (medical PAT apparatus) is described below.

Figure 12:
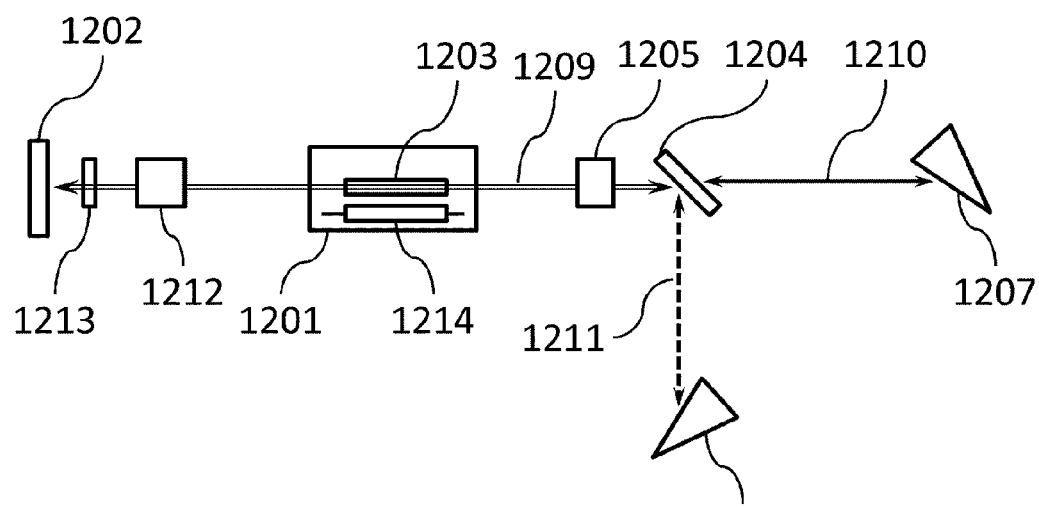
FIG. 12 is a schematic view of embodiment 3.

FIG. 12 is a schematic view illustrating a laser apparatus incorporated in a medical PAT apparatus. This laser apparatus is an alexandrite laser using a flash lamp 1214 as an excitation source and is capable of generating laser oscillation with wavelengths of 800 nm and 755 nm. The laser apparatus is driven by excitation light at a repetitive frequency of 20 Hz. The output power is 200 mJ/pulse. The alexandrite laser has the following configuration. The flash lamp 1214 for generating excitation light, together with an alexandrite crystal 1203, is disposed in a chamber 1201. A Q-sw for giant pulse oscillation comprising a Pockels cell 1212 and a $\lambda/4$ wave plate 1213 is disposed on a common optical path 1209. A resonance optical path selecting portion comprises a Pockels cell 1205. The laser apparatus also includes an output mirror 1202, a polarizer 1204 serving as an optical path branching portion, a first reflective prism 1207 as a reflecting portion of a first optical path branch 1210 forming a 755-nm wavelength resonator, and a second reflective prism 1208 as a reflecting portion of a second optical path branch 1211.

The alexandrite laser is excited by the flash lamp and generates high power pulse oscillation by Q-sw drive. The polarization direction of a light beam oscillated is p-polarization which is in the plane of the drawing sheet.

The polarizer 1204 transmits p-polarized light and reflects s-polarized light. The reflective prism 1207 is positioned to form a Brewster angle relative to incident light. The reflective prism 1207 has a reflecting plane provided with a dielectric reflective coating for reflecting light having a wavelength of 800 nm. The reflective prism 1208 has an incidence plane provided with a dielectric anti-reflection coating with respect to light having a wavelength of 755 nm and a reflecting plane provided with a dielectric reflective coating for reflecting light having a wavelength of 755 nm. The Pockels cell 1205 for resonance optical path selection is applied with a voltage causing the polarization of incident light to rotate by $\lambda/2$, thereby selecting a resonance optical path.

Using the laser apparatus described above with a first pulse at 800 nm and a second pulse at 755 nm, laser oscillation was generated with alternate change in wavelength on a pulse-by-pulse basis. Before the first pulse oscillation, voltage applied to the Pockels cell 1205 for resonance optical path selection was turned OFF. After irradiation by the flash lamp 1214, the Q-sw was driven at the time the population inversion density of the alexandrite crystal reached a sufficiently high level. At that time, the polarization direction of a light beam inside the resonator was p-polarization. Polarized light having passed through the Pockels cell 1205 maintained p-polarization. The light passed through the polarizer 1204 and the first optical path branch to resonate and was then emitted as oscillation of laser light having a wavelength of 800 nm from the output mirror 1202.

After the laser oscillation, voltage was applied to the Pockels cell 1205 before irradiation by the flash lamp for the next pulse oscillation and the voltage ON-state was maintained until completion of the second laser pulse oscillation. The polarization of a light beam passing through the Pockels cell was rotated 90° and resulting s-polarized light was reflected by the polarizer 1204. The light thus reflected passed through the second optical path branch to resonate and was then emitted as oscillation of laser light having a wavelength of 755 nm from the output mirror 1202.

The output light beams thus obtained were measured for their wavelengths and energy on a pulse-by-pulse basis. Light having a wavelength of 800 nm and light having a wavelength of 755 nm were alternately emitted, and the energy stability of each pulse was substantially the same as with an alexandrite laser for fixed wavelength oscillation with no resonator branching. Thus, very stable oscillation was obtained.

The present laser has no mechanical driving component in a system associated with wavelength change. Therefore, wavelength reproducibility and oscillation energy output stability are very high. As a result, the present laser is excellent in long-term stability with a very low possibility that an energy drop or a like problem arises due to misalignment or the like. The laser is constructed using optical components each having a high energy damage threshold and incurs a relatively small optical energy loss at each optical component though the polarizer 1204 incurs an energy loss of not more than 1%. Therefore, high irradiation energy was obtained as an output energy of 200 mJ/pulse.

The present laser apparatus was incorporated in a fixed type PAT apparatus configured to scan a PAT probe over a part of a fixed living body, the PAT probe having an ultrasound element and a laser beam emitting portion which were integrated with each other. A measurement sample used was a living body imitation sample having a blood vessel in which oxidized type hemoglobin limitation and reduced type hemoglobin imitation were present and which was located at a depth of 30 mm from a living body surface. The sample was scanned with a repetitive frequency of 20 Hz. In the measurement, switching was made between 700-nm wavelength and 850-nm wavelength on a pulse-by-pulse basis to acquire functional information characteristic of each wavelength. The use of the laser apparatus according to the present invention made it possible to acquire highly precise functional information with a little effect on received signals by a position displacement or a measurement time lag.

Embodiment 4

One embodiment of a laser apparatus for use in a medical photoacoustic tomography apparatus (medical PAT apparatus) is described below.

Figure 13:
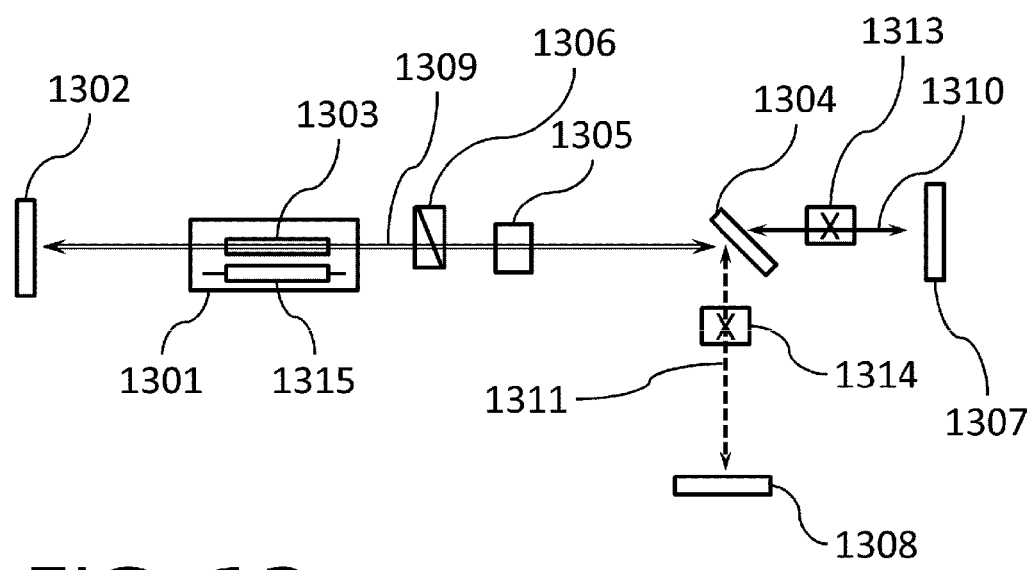
FIG. 13 is a schematic view of embodiment 4.

FIG. 13 is a schematic view illustrating a laser apparatus incorporated in a medical PAT apparatus. This laser apparatus is an alexandrite laser using a flash lamp 1315 as an excitation source and is capable of generating laser oscillation with wavelengths of 800 nm and 755 nm. The laser apparatus is driven by excitation light at a repetitive frequency of 20 Hz. The output power is 200 mJ/pulse. The alexandrite laser has the following configuration. The flash lamp 1315 for generating excitation light, together with an alexandrite crystal 1303, is disposed in a chamber 1301. The laser apparatus also includes an output mirror 1302, a polarizer 1304 serving as an optical path branching portion, a Pockels cell 1305 serving as a resonance optical path selecting portion and a Q-sw both, and a polarizer 1306 as a component of the Q-sw. The laser apparatus also includes a reflecting member 1307 of a first optical path branch 1310 forming a 800-nm wavelength resonator, a reflecting member 1308 of a second optical path branch 1311 forming a 755-nm wavelength resonator, and a common optical path 1309. The laser apparatus further includes a first shield member 1313 disposed on the first optical path branch 1310, and a second shield member 1314 disposed on the second optical path branch 1311.

The polarizer 1306 transmits p-polarized light. In the embodiment shown, the polarization direction of p-polarized light is in the plane of the drawing sheet, while the polarization direction of s-polarized light is perpendicular to the plane of the drawing sheet.

The voltage to be applied to the Pockels cell 1305 is a voltage that causes the polarization of incident light to rotate by 90°. The reflecting member 1307 has a reflecting plane provided with a narrowband dielectric reflective coating for reflecting light having a wavelength of 800 nm. The reflecting member 1308 has a reflecting plane provided with a narrowband dielectric reflective coating for reflecting light having a wavelength of 755 nm.

Using the laser apparatus described above with a first pulse at 800 nm and a second pulse at 755 nm, laser oscillation was generated with alternate change in wavelength on a pulse-by-pulse basis. Before the first pulse oscillation, the first shield member 1313 was opened and the second shield member 1314 closed. Further, before irradiation by the flash lamp 1315, the voltage was applied to the Pockels cell 1305, followed by irradiation by the flash lamp 1315. A light beam having p-polarization generated upon irradiation by the flash lamp becomes incident on the Pockels cell and the polarization thereof is rotated into s-polarized light. Then, the light beam is reflected by the polarizer 1304 (polarization beam splitter). However, the light beam is shielded by the second shield member. Therefore, the light beam is unable to resonate, with the result that the population inversion density of the alexandrite crystal is raised. When the voltage applied to the Pockels cell 1305 is turned OFF at that timing, the polarized state of the light beam passing through the Pockels cell is maintained as p-polarization. For this reason, the light beam having passed through the polarization beam splitter 1304 passes through the first optical path branch 1310 to resonate in a resonator having a high Q-value which comprises the output mirror 1302 and the reflecting member 1307. Thus, oscillation of laser light having a wavelength of 800 nm is generated.

After the first pulse oscillation, the first shield member 1313 was closed and the second shield member 1314 opened before irradiation by the flash lamp 1315 for the second pulse. Further, before irradiation by the flash lamp 1315, the Pockels cell 1305 was maintained in a state free of voltage application, followed by irradiation by the flash lamp 1315. A light beam generated upon irradiation by the flash lamp maintains p-polarization even after having passed through the Pockels cell and passes through the polarization beam splitter 1304. However, the light beam is shielded by the second shield member. Therefore, the light beam is unable to resonate, with the result that the population inversion density of the alexandrite crystal is raised. When voltage application to the Pockels cell 1305 is turned ON at that timing, the polarized state of the light beam is rotated into s-polarization by the Pockels cell 1305. The light beam having been reflected by the polarization beam splitter 1304 passes through the second optical path branch 1311 to resonate in a resonator having a high Q-value which comprises the output mirror 1302 and the reflecting member 1308. Thus, oscillation of laser light having a wavelength of 755 nm is generated.

The laser apparatus having the present configuration is capable of generating two-wavelength pulse oscillation by using the Pockels cell serving as the Q-sw and the resonance optical path selecting portion both.

The output light beams thus obtained were measured for their wavelengths and energy on a pulse-by-pulse basis. Light having a wavelength of 800 nm and light having a wavelength of 755 nm were alternately emitted, and the energy stability of each pulse was substantially the same as with an alexandrite laser for fixed wavelength oscillation with no resonator branching. Thus, very stable oscillation was obtained.

The present laser has no mechanical driving component in a system associated with wavelength change. Therefore, wavelength reproducibility and oscillation energy output stability are very high. As a result, the present laser is excellent in long-term stability with a very low possibility that an energy drop or a like problem arises due to misalignment or the like. The laser is constructed using optical components each having a high energy damage threshold and incurs a relatively small optical energy loss at each optical component though the polarizer 1204 incurs an energy loss of not more than 1%. Therefore, high irradiation energy was obtained as an output energy of 200 mJ/pulse. Further, there is no need to add any special component to the resonance optical path selecting portion and, hence, the present laser has advantages that the resonator length is rendered compact and the cost reduced.

The present laser apparatus was incorporated in a fixed type PAT apparatus configured to scan a PAT probe over a part of a fixed living body, the PAT probe having an ultrasound element and a laser beam emitting portion which were integrated with each other. A measurement sample used was a living body imitation sample having a blood vessel in which oxidized type hemoglobin limitation and reduced type hemoglobin imitation were present and which was located at a depth of 30 mm from a living body surface. The sample was scanned with a repetitive frequency of 20 Hz. In the measurement, switching was made between 700-nm wavelength and 850-nm wavelength on a pulse-by-pulse basis to acquire functional information characteristic of each wavelength. The use of the laser apparatus according to the present invention made it possible to acquire highly precise functional information with a little effect on received signals by a position displacement or a measurement time lag.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-226959, filed on Oct. 14, 2011, which is hereby incorporated by reference herein in its entirety.

The invention claimed is:

1. A laser apparatus capable of selecting a wavelength of light to be outputted from a plurality of wavelengths, comprising:
    an output mirror;
    a reflecting unit having at least a first reflecting plane and a second reflecting plane, each of said first and second reflecting planes forming one of two resonators with said output mirror;
    a branching unit comprising a polarizer, said branching unit being configured to form a common optical path common to two optical paths in said two resonators which has an end defined by said output mirror, wherein a first optical path has an end defined by said first reflecting plane and a second optical path has an end defined by said second reflecting plane and is different from said first optical path;
    a laser medium disposed in said common optical path;
    a selecting unit configured to select, from said first and second optical paths, an optical path which corresponds to a wavelength of light to be outputted; and
    shielding that has a first shield member in said first optical path and a second shield member in said second optical path, said first and second shield members shielding said first and second optical paths independently;
    wherein, in a first case in which a laser oscillation of a first wavelength is generated using said common optical path and said first optical path, said selecting unit selects said second optical path until a time at which an emission output of the laser oscillation is maximized with said first shield member open and said second shield member closed and selects said first optical path after the time at which the emission output of the laser oscillation is maximized with said first shield member open and said second shield member closed.

2. The laser apparatus according to claim 1, wherein said selecting unit comprises a polarization rotating member which is provided on said common optical path and selects one of said first and second optical paths by changing a polarization direction of light passing through said polarization rotating member.

3. The laser apparatus according to claim 2, wherein said polarization rotating member comprises a Pockels cell.

4. The laser apparatus according to claim 1, wherein said selecting unit comprises a Pockels cell which also serves as a Q-switch for pulse oscillation in said resonators and which is configured to select one of said first and second optical paths by changing a polarization direction of light passing through said Pockels cell in accordance with voltage applied thereto.

5. A method of controlling a laser apparatus capable of selecting a wavelength of light to be outputted from a plurality of wavelengths,
    the laser apparatus including an output mirror, a reflecting unit having at least a first reflecting plane and a second reflecting plane, each of the first and second reflecting planes forming one of two resonators with the output mirror, a branching unit comprising a polarizer and configured to form a common optical path common to two optical paths in the two resonators which has an end defined by the output mirror, of which a first optical path has an end defined by the first reflecting plane and a second optical path has an end defined by the second reflecting plane and is different from the first optical path, and a laser medium disposed in the common optical path, the method comprising
    a selecting step in which a selecting unit selects, from the first and second optical paths, an optical path which corresponds to a wavelength of light to be outputted,
    wherein, in said selecting step, in a first case in which a laser oscillation is generated using the common optical path and the first optical path, the second optical path is selected until a time at which an emission output of the laser oscillation is maximized with a first shield member in the first optical path open and a second shield member in the second optical path closed and the first optical path is selected at the time at which the emission output of the laser oscillation is maximized with the first shield member in the first optical path open and the second shield member in the second optical path closed.

6. The laser apparatus according to claim 1,
    wherein said polarizer of said branching unit makes light polarized in a first direction pass through said polarizer and reflects light polarized in a second direction which is different from the first direction, and
    wherein said branching unit guides the light polarized in the first direction into said first optical path and the light polarized in the second direction into the second optical path.

7. The laser apparatus according to claim 6,
    wherein said selecting unit is arranged between said branching unit and said laser medium,
    wherein said selecting unit comprises a first polarizer which makes the light polarized in the first direction pass through said first polarizer, and a polarization rotating member, said polarizer being arranged nearer to said laser medium than said polarization rotating member,
    wherein said polarization rotating member of said selecting unit selects said second optical path by rotating the light polarized in the first direction into the second direction, and selects said first optical path by keeping the light polarized in the first direction which has passed through said polarizer.

8. The laser apparatus according to claim 7, wherein, in the first case, said polarization rotating member rotates the light polarized in the first direction which passes through said polarizer into the second direction until the time at which the emission output of the laser oscillation is maximized, and keeps the light polarized in the first direction after the time at which the emission output of the laser oscillation is maximized.

9. The laser apparatus according to claim 7, further comprising a driver,
wherein said polarization rotating member comprises a Pockels cell which is driven by said driver, and
wherein said driver causes said Pockels cell to rotate the light polarized in the first direction into the second direction by supplying a voltage.

10. The laser apparatus according to claim 9, wherein, in the first case, said driver supplies the voltage to said Pockels cell until the time at which the emission output of the laser oscillation is maximized and shuts down the voltage after the time at which the emission output of the laser oscillation is maximized.

11. The laser apparatus according to claim 1, wherein, in a second case, in which a laser oscillation of a second wavelength that is different from the first wavelength is generated using said common optical path and said second optical path, said selecting unit selects said first optical path until the time at which the emission output of the laser oscillation is maximized with said first shield member closed and said second shield member open and selects said second optical path after the time at which the emission output of the laser oscillation is maximized with first shield member closed and said second shield member open.

12. The laser apparatus according to claim 11,
wherein said polarizer of said branching unit causes light polarized in a first direction to pass through said polarizer, and reflects light polarized in a second direction which is different from the first direction, and
wherein said branching unit guides the light polarized in the first direction into first optical path and the light polarized in the second direction into said second optical path.

13. The laser apparatus according to claim 12,
wherein said selecting unit is arranged between said branching unit and said laser medium,
wherein said selecting unit comprises a first polarizer which makes the light polarized in the first direction pass through said first polarizer, and a polarization rotating member, said polarizer being arranged nearer to said laser medium than said polarization rotating member,
wherein said polarization rotating member of said selecting unit selects said second optical path by rotating the light polarized in the first direction into the second direction, and selects said first optical path by keeping the light polarized in the first direction which has passed through said polarizer.

14. The laser apparatus according to claim 13,
wherein, in the first case, said polarization rotating member rotates the light polarized in the first direction which passes through said polarizer into the second direction until the time at which the emission output of the laser oscillation is maximized, and keeps the light polarized in the first direction after the time at which the emission output of the laser oscillation is maximized; and wherein, in the second case, said polarization rotating member keeps the light polarized in the first direction which passes through said polarizer until the time at which the emission output of the laser oscillation is maximized, and rotates the light polarized in the first direction which passes through said polarizer into the second direction after the time at which the emission output of the laser oscillation is maximized.

15. The laser apparatus according to claim 13, further comprising a driver,
wherein said polarization rotating member comprises a Pockels cell which is driven by said driver, and
wherein said driver causes said Pockels cell to rotate the light polarized in the first direction into the second direction by supplying a voltage.

16. The laser apparatus according to claim 15,
wherein, in the first case, said driver supplies the voltage to said Pockels cell until the time at which the emission output of the laser oscillation is maximized and shuts down the voltage after the time at which the emission output of the laser oscillation is maximized; and
wherein, in the second case, said driver does not supply the voltage to said Pockels cell until the time at which the emission output of the laser oscillation is maximized and supplies the voltage to said Pockels cell after the time at which the emission output of the laser oscillation is maximized.

17. The method of controlling a laser apparatus according to claim 5, wherein, in a second case in which a laser oscillation of a second wavelength that is different from the first wavelength is generated using the common optical path and the second optical path, the first optical path is selected until the time at which the emission output of the laser oscillation is maximized with the first shield member in the first optical path closed and the second shield member in the second optical path opened and the second optical path is selected after the time at which the emission output of the laser oscillation is maximized with the first shield member in the first optical path closed and the second shield member in the second optical path opened.

18. A PAT apparatus comprising said laser apparatus according to claim 1, and a PAT probe.

19. A laser apparatus comprising:
an output mirror;
a reflecting unit having at least a first reflecting plane and a second reflecting plane, each of said first and second reflecting planes forming one of two resonators with said output mirror;
a branching unit configured to form a common optical path common to two optical paths in said two resonators which has an end defined by said output minor, wherein a first optical path has an end defined by said first reflecting plane and a second optical path has an end defined by said second reflecting plane and is different from said first optical path;
a laser medium disposed in said common optical path; and
a selecting unit configured to select, from said first and second optical paths, an optical path which corresponds to a wavelength of light to be outputted,
wherein said first optical path corresponds to a first wavelength and the second optical path corresponds to a second wavelength different from the first wavelength; and
wherein, in a first case in which a laser oscillation of the first wavelength is generated using said common optical path and said first optical path, said selecting unit selects said second optical path until a first predetermined time without oscillating the laser in the second wavelength, and selects said first optical path and oscillates the laser in the first wavelength after the first predetermined time.

20. The laser apparatus according to claim 19, wherein, in a second case, in which a laser oscillation of said second wavelength is generated using said common optical path and said second optical path, said selecting unit selects said first optical path without oscillating the laser in the first wavelength until a second predetermined time, and selects said second optical path and oscillates the laser in the second wavelength after the second predetermined time.

21. The laser apparatus according to claim 19, wherein the first predetermined time is a time at which the emission output of the laser oscillation is maximized.

22. The laser apparatus according to claim 20, wherein the second predetermined time is a time at which the emission output of the laser oscillation is maximized.

* * * * *